United States Patent [19]

Mizusaki et al.

[11] 4,446,474
[45] May 1, 1984

[54] ION SENSOR FET WITH SURFACE TREATED METAL GATE

[75] Inventors: Takashi Mizusaki, Tokyo; Tadayuki Matsuo, Sendai; Masayoshi Esashi, Sendai; Hiroshi Abe, Sendai, all of Japan

[73] Assignee: Olympus Optical Co. Ltd., Japan

[21] Appl. No.: 163,792

[22] Filed: Jun. 27, 1980

[30] Foreign Application Priority Data

Mar. 19, 1980 [JP] Japan ............................ 55-33898
Mar. 19, 1980 [JP] Japan ............................ 55-33899

[51] Int. Cl.³ ................... H01L 29/78; G01N 27/30
[52] U.S. Cl. ................................. 357/25; 357/23; 357/54; 204/1 T; 204/419
[58] Field of Search ............... 357/23 I, 25, 54, 52; 204/1 T, 419

[56] References Cited

U.S. PATENT DOCUMENTS

| 3,831,432 | 8/1974 | Cox ........................................ 357/25 |
| 4,180,771 | 12/1979 | Guckel .................................. 357/25 |
| 4,273,636 | 6/1981 | Shimada et al. ...................... 357/25 |
| 4,302,530 | 11/1981 | Zemel . | |
| 4,305,802 | 12/1981 | Koshiishi ............................. 357/25 |

OTHER PUBLICATIONS

Esashi et al., IEEE Trans. on Biomedical Engineering, (BME-25, No. 2, Mar. 1978), pp. 184-192.
Moss et al., IEEE Trans. on Biomedical Engineering, (BME25, No. 1), Jan. 1978, pp. 49-54.
Esashi et al., Suppl. to Journal of the Japan Society of Applied Physics, vol. 44, 1975, pp. 339-343.

Primary Examiner—William D. Larkins
Attorney, Agent, or Firm—Parkhurst & Oliff

[57] ABSTRACT

An ion sensor and more particularly ion sensitive field effect transistor comprising an inorganic film, and an impurity layer formed in at least surface layer of said inorganic film by thermal diffusion or ion implantation.

3 Claims, 21 Drawing Figures

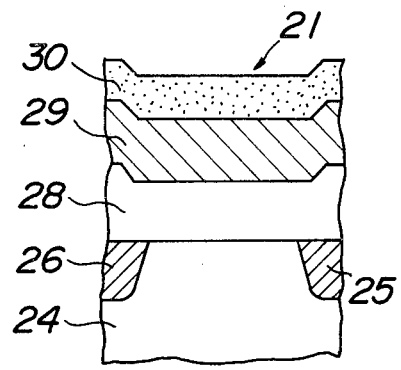
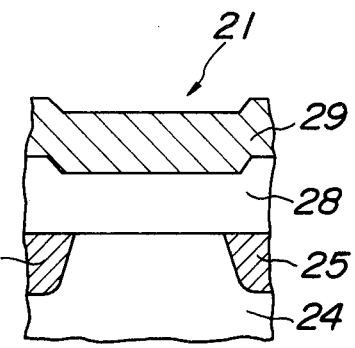
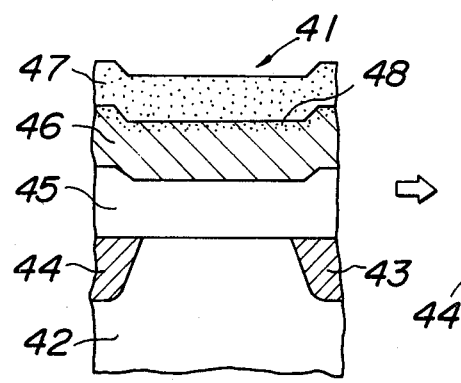
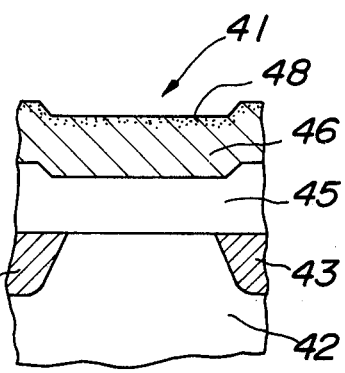
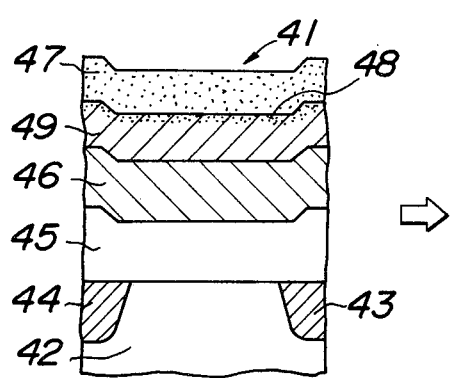
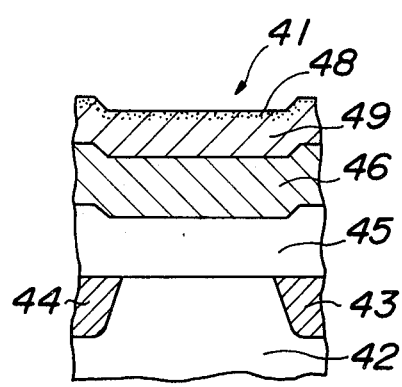

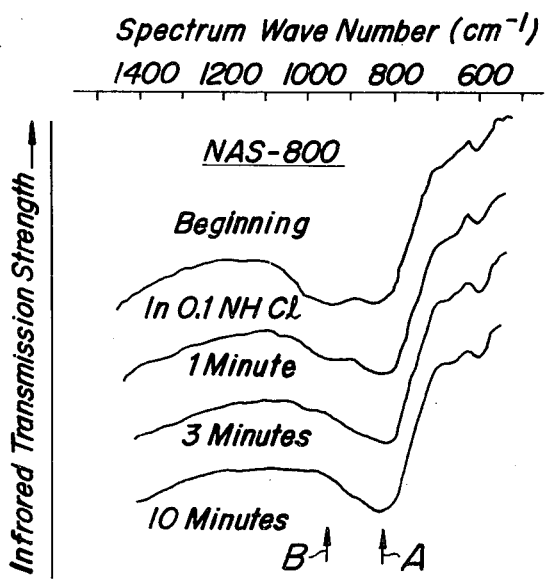
FIG_11A
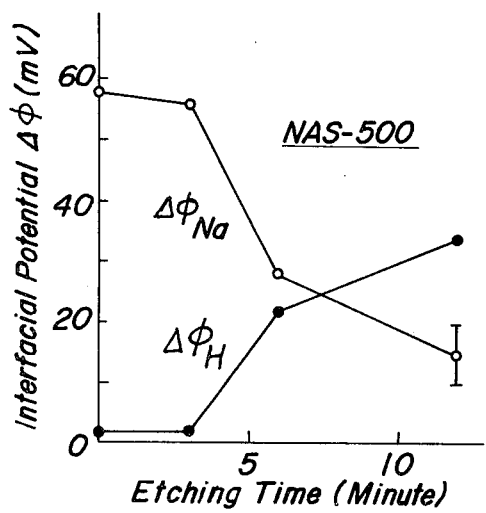
FIG_11B
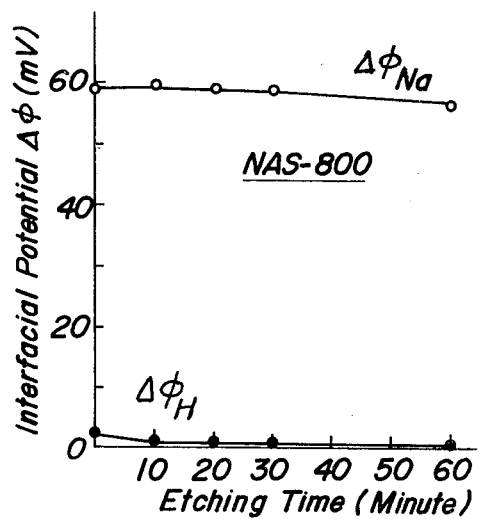
FIG_11C

ION SENSOR FET WITH SURFACE TREATED METAL GATE

BACKGROUND OF THE INVENTION

1. Field of the Invention

This invention relates to an ion sensor and more particularly to an ion sensitive field effect transistor for measuring a given ion concentration in an electrolyte.

2. Description of the Prior Art

In such kind of ion sensitive field effect transistor, an insulating gate type field effect transistor comprises a chemically selective film containing an ion exchange substance, enzyme or the like and formed on a gate portion thereof, the chemically selective film being operative to detect the presence or the like of a given substance acting on a given active amount of ion or enzyme in an electrolyte.

In a first example of an ion sensitive field effect transistor which has heretofore been proposed, a chemically selective film is formed on that portion of an insulating layer which is superimposed on a channel region and that portion of the insulating layer which is not covered with the chemically selective film is covered with a solution impermeable film. When such conventional ion sensitive field effect transistor is used, the chemically selective film is brought into contact with a test liquid. In this case, the insulating layer covering the surface of a semiconductor substrate is hydrated through the chemically selective film and a given cation, for example, $H^+$, $Na^+$ or the like is penetrated into the insulating layer, thereby inducing a gate leak failure or the like and hence inducing a formidable obstacle in the case of measuring stability and reproductive property of the ion sensitive field effect transistor. In addition, the solution impermeable film covering that portion of the insulating layer which is not covered with the chemically selective film and formed of epoxy resin becomes swollen after the lapse of time, thereby exerting bad influence to the stability of the ion sensitive field effect transistor.

In a second example of an ion sensitive field effect transistor which has heretofore been proposed, a silicon nitride layer and an ion sensitive layer are suerpimposed one upon the other on that portion of an insulating layer which is opposed to a channel region to form a gate portion and the outer surface other than this gate portion is covered with an insulating resin layer. In such conventional ion sensitive field effect transistor, it is difficult to make the insulating resin layer covering the surface other than the gate portion thin without forming any pin hole therein. In addition, the insulating resin layer is gradually swollen in a test liquid, thereby degrading the stability and durability of the ion sensitive field effect transistor.

In a third example of an ion sensitive field effect transistor which has heretofore been proposed, a gate portion as a whole is covered with an oxide film and a surface stabilizing film superimposed one upon the other and on that side of the surface stabilizing film which is opposed to drain and source diffusion regions is formed an ion sensitive film.

In all of the above mentioned conventional ion sensitive field effect transistors, the chemically selective film of the first example, ion sensitive layer of the second example and ion sensitive film of the third example are superimposed on the insulating layer, silicon nitride layer and surface stabilizing film by chemical vapor deposition, dipping or the like, respectively. As a result, the ion sensitive film, for example, is not sufficiently adhered to the surface stabilizing film and hence becomes easily separated or effluent from the latter, thereby exposing the surface stabilizing film and hence losing the ability of the ion sensitive field effect transistor within a short time.

SUMMARY OF THE INVENTION

An object of the invention, therefore, is to provide an ion sensor which can eliminate the above mentioned various drawbacks which have been encountered with the prior art techniques, which can hold the ion sensitive substance in a stable manner and which can be used for a long time in a stable manner.

Another object of the invention is to provide an ion sensitive field effect transistor which has a large transfer conductance and hence can obtain a sufficiently large grain and which does not change a threshold value voltage.

A feature of the invention is the provision of an ion sensor comprising an inorganic film, and an impurity layer formed in at least surface layer of said inorganic film and containing an impurity sensitive to a given ion, said impurity layer being operative as an ion sensitive region when it makes contact with a test substance.

Further objects and features of the invention will be fully understood from the following detailed description with reference to the accompanying drawings, wherein:

BRIEF DESCRIPTION OF THE DRAWINGS

FIGS. 4A and 4B are enlarged diagrammatic cross-sectional views of the gate portion of the ion sensitive field effect transistor shown in FIGS. 3A and 3B and illustrating the drawback which has been encountered therewith;

FIGS. 5A and 5B are diagrammatic cross-sectional views of essential parts of one embodiment of an ion sensitive field effect transistor according to the invention manufactured by thermal diffusion;

FIGS. 6A and 6B are diagrammatic cross-sectional views of essential parts of another embodiment of an ion sensitive field effect transistor according to the invention manufactured by thermal diffusion;

FIG. 11A is a graph illustrating an infrared absorption characteristic of an ion sensitive field effect transistor;

FIG. 11B is a graph illustrating an ion characteristic of a conventional ion sensitive field effect transistor; and FIG. 11C is a graph illustrating an ion characteristic of an ion sensitive field effect transistor according to the invention.

DETAILED DESCRIPTION OF THE PREFERRED EMBODIMENTS

Figure 1:
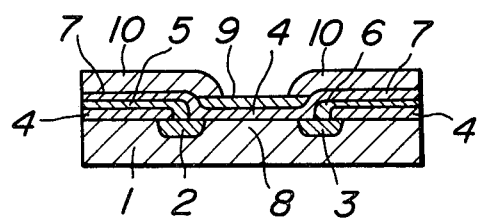
FIG. 1 is a diagrammatic cross-sectional view of a first example of a conventional ion sensitive field effect transistor.

FIG. 1 is a diagrammatic cross-sectional view of a first example of a conventional ion sensitive field effect transistor. The ion sensitive field effect transistor shown in FIG. 1 comprises a p type silicon semiconductor substrate 1 which is provided on its surface with a source diffusion surface region 2 and a drain diffusion surface region 3 spaced apart from each other. The surface of the substrate 1 is covered with an insulating layer 4 formed of silicon dioxide ($SiO_2$). To the source and drain regions 2 and 3 are connected conductors 5 and 6 through holes formed in the insulating layer 4, respectively. These conductors 5, 6 are covered with an insulating layer 7. That portion of the insulating layer 4 which is opposed to a channel region 8 is covered with a chemically selective film 9, whereas that portion of the insulating layer 7 which is not covered with the chemically selective film 9 is covered with a solution impervious film 10.

When the ion sensitive field effect transistor constructed as above described is used, the chemically selective film 9 is brought into contact with a test liquid. As a result, the test liquid is penetrated through the film 9 into the insulating layer 4 to cause it to be hydrated.

Thus, a given cation, for example, $H^+$, $Na^+$ or the like is penetrated into the insulating layer 4, thereby inducing a gate leak failure or the like and hence inducing a formidable obstacle in the case of measuring stability and reproductive property of the ion sensitive field effect transistor. In addition, in the solution impermeable film 10 formed of epoxy resin, the epoxy resin is swollen after the lapse of time, thereby exerting bad influence of the stability of the ion sensitive field effect transistor.

Figure 2A:
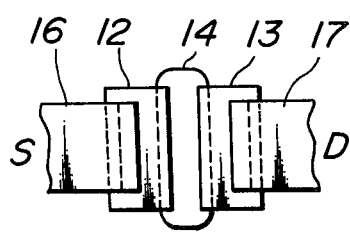
FIG. 2A is a diagrammatic plan view of a second example of a conventional ion sensitive field effect transistor.
Figure 2B:
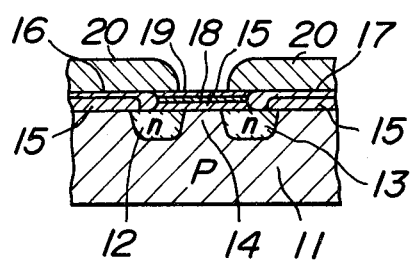
FIG. 2B is its diagrammatic cross-sectional view.

FIGS. 2A and 2B show a construction of a second example of the conventional ion sensitive field effect transistor. FIG. 2A is a diagrammatic plan view and FIG. 2B is its cross-sectional view. This ion sensitive field effect transistor comprises a p type silicon semiconductor substrate 11 which is provided on its surface with two n-type surface regions 12 and 13 formed by diffusion, for example, and operative as a source S and a drain D, respectively. Between these two n type surface regions 12 and 13 is formed a channel region 14. On the surface of the semiconductor substrate 11 is formed an insulating layer 15 formed of $SiO_2$ and provided thereon with conductors 16 and 17 vapor deposited thereon. These conductors 16 and 17 are electrically connected through holes formed in the insulating layer 15 to the source and drain surface regions 12 and 13, respectively. On that insulating layer 15 which is disposed on the channel region 14 are superimposed a silicon nitride ($Si_3N_4$) layer 18 and an ion sensitive layer 19 one upon the other to form a gate portion, the outer surface other than this gate portion being covered with an insulating resin layer 20. This ion sensitive field effect transistor is provided on the insulating layer 15 with the silicon nitride layer 18, so that this portion can be made stable. But, it is difficult to make the insulating resin layer 20 covering the surface other than the gate portion thin without forming any pin hole. In addition, the insulating resin layer 20 is gradually swollen in a test liquid, thereby degrading the stability and durability of the ion sensitive field effect transistor.

Figure 3A:
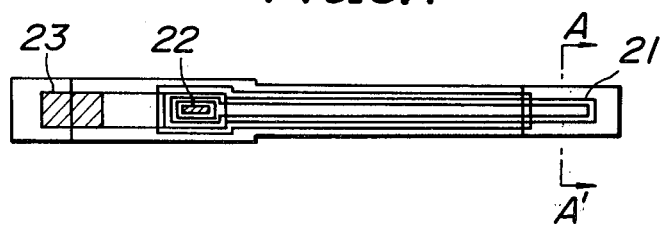
FIG. 3A is a diagrammatic plan view of a third example of a conventional ion sensitive field effect transistor.
Figure 3B:
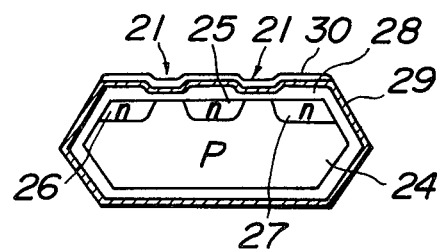
FIG. 3B is a section on line A—A' of FIG. 3A.

FIGS. 3A and 3B show a construction of a third example of a conventional ion sensitive field effect transistor. FIG. 3A is a plan view and FIG. 3B is a section on line A—A' of FIG. 3A. This ion sensitive field effect transistor is of elongate one having a width of 0.4 mm and a length of 3 to 4 mm, for example. The ion sensitive field effect transistor is provided at its one end portion with a gate portion 21 and at the other end portion with drain and source contacts 22 and 23. The gate portion 21 comprises a silicon substrate 24 provided thereon with a drain diffusion region 25 and source diffusion regions 26, 27. The gate portion 21 as a whole is covered with an oxide film 28 and a surface stabilizing film 29 superimposed one upon the other. On that side of the surface stabilizing film 29 which is opposed to the drain and source diffused regions is formed an ion sensitive film 30. The ion sensitive film 30 may be composed of a multi-composition glass film having a composition of NAS 11-18 (11 mol% of $Na_2O$, 18 mol% of $Al_2O_3$ and 71 mol% of $SiO_2$) for $Na^+$ ion and may be composed of polyvinyl chloride film including valinomycin diffused thereinto for $K^+$ ion. This conventional ion sensitive field effect transistor having total surface covered with the oxide film 28 and surface stabilizing film 29 can improve its stability and durability.

In the above described conventional ion sensitive field effect transistors shown in FIGS. 1, 2 and 3, the chemically selective film 9, ion sensitive layer 19 and ion sensitive film 30 are superimposed on the insulating layer 4, silicon nitride layer 18 and surface stabilizing film 29 by means of chemical vapor deposition, dipping or the like, respectively.

The use of such measure of superimposing the ion selective film on the lower layer provides the following disadvantage. For example, as shown in FIG. 4A which shows in an enlarged scale the gate portion of the ion sensitive field effect transistor shown in FIG. 3B, the ion sensitive film 30 is not sufficiently adhered to the surface stabilizing film 29, so that the ion sensitive film 30 becomes easily separated or effluent from the surface stabilizing film 29. As a result, the surface stabilizing film 29 is exposed in the gate portion 21 as shown in FIG. 4B, thereby losing the ability of the ion sensitive field effect transistor within a short time.

In this case, if the surface stabilizing film 29 is formed, for example, of $Si_3N_4$ having an ability of $H^+$ ion sensitive film, the ion sensitive field effect transistor operated at first as the $Na^+$ or $K^+$ ion sensor gradually loses its ability and finally is changed into $H^+$ ion sensor.

In the ion sensitive field effect transistor considered as a field effect transistor element, the drain current $I_D$ in the saturation region ($V_G - V_T^* + \psi < V_D$) when the source potential is made zero is given by $$I_D = \frac{1}{2}\left(\frac{\mu\epsilon W}{tL}\right)(V_G - V_T^* + \psi)^2 \quad (1)$$

where

- $\mu$: Surface mobility of electron (or positive hole)
- $\epsilon$: Dielectric constant of gate insulating film
- $t$: Thickness of gate insulating film
- $W$: Width of gate channel
- $L$: Length of gate channel
- $V_G$: Gate (reference electrode) potential
- $\psi$: Interfacial potential between sensitive film and electrolyte
- $V_T^*$ (more precisely $V_T^* - \psi$):
  Gate threshold value voltage $V_T^*$ is given by $$V_T^* = \phi_{cs} + 2\phi_f + E_{ref} - (Q_s + Q_B)/C_o \quad (2)$$

where

- $\phi_{cs}$: Work function difference between sensitive film and semiconductor
- $\phi_f$: Fermi potential of silicon (substrate)
- $E_{ref}$: Interfacial potential between reference electrode and electrolyte
- $Q_s$: Charge density in gate insulating film
- $Q_B$: Charge density in surface depletion layer
- $C_o$: Capacity of gate insulating film.

In the above mentioned conventional ion sensitive field effect transistor considered as the field effect transistor element, the use of the construction in which the ion selective film is merely superimposed on the lower layer provides a number of disadvantages. In the first place, defects are induced near the ion sensitive film 30-surface stabilizing film 29 interface. Secondly, if a surplus electric charge is accumulated, the term $Q_s$ of the above mentioned equation (2) is changed and hence the gate threshold value voltage $V_T^*$ becomes changed. Finally, the film of the gate portion as a whole becomes large in thickness, so that the transfer conductance gm (which is a parameter representing the gain of the field effect transistor and proportional to the term ($\mu\epsilon W/tL$) of the above mentioned equation (1)) is degraded and hence it is impossible to obtain a sufficiently large gain.

FIGS. 5A and 5B are diagrammatic cross-sectional views of essential parts of one embodiment of an ion sensitive field effect transistor according to the invention illustrating a method of manufacturing the same according to the invention. FIG. 5A shows only a gate portion of the ion sensitive field effect transistor in an enlarged scale. In the first place, in a semiconductor substrate 42 having a thickness on the order of 200 μm are formed a drain diffusion region 43 and a source diffusion region 44.

On the surface of the substrate 42 is formed a gate insulating film 45. Then, on the gate insulating film 45 inclusive of at least gate portion is formed a surface stabilizing film 46 having a thickness on the order of 500 Å to 2,000 Å. This surface stabilizing film 46 may be formed of an inorganic insulating material having an excellent ion impermeability, for example, a composition selected from the group consisting of silicon nitride ($Si_3N_4$), silicon oxy nitride (SiOxNy), oxide of aluminum (Al) or tantalum (Ta), nitride of aluminum or tantalum and a mixture of said oxide and nitride. The surface stabilizing film 46 may be formed on the gate insulating film 45 by means of a chemical vapor deposition, sputtering, electron beam vapor deposition or the like. Then, on the surface stabilizing film 46 inclusive of at least gate portion is formed a diffusion source film 47 having a thickness on the order of 500 Å to 10,000 Å and operative to react with substance constituting the surface stabilizing film 46 to form an ion exchange site sensitive to a given ion. Then, at least gate portion 41 is heated at a temperature of 600° to 1,000° C. with the aid of resistance heating furnace, infrared ray lamp, YAG laser, $CO_2$ laser so as to thermally diffuse a part of the composition of the diffusion source 47 into the surface stabilizing film 46, thereby forming an impurity layer 48 operative as an ion sensitive region and having a thickness on the order of several tens Å to several hundreds Å.

The diffusion source 47 may be formed of compounds which are different in kind dependent on the kind of the ion sensor aimed at and on the kind of the surface stabilizing film 46. In the case of the $Na^+$ ion and $K^+$ ion sensor, use may be made of compounds shown in the following Table 1, for example.

TABLE 1

| | Kind of surface stabilizing film 46 | | | |
|---|---|---|---|---|
| | Oxide, Nitride of Si | Oxide, Nitride of Al | Oxide, Nitride of Ta | $SiO_2 + Al_2O_3$ |
| Compound of diffusion source 47 | $Na_2O$ or $Li_2O$ and $Al_2O_3$ | $Na_2O$ or $Li_2O$ and $SiO_2$ | $Na_2O$ or $Li_2O$, $Al_2O_3$ and $SiO_2$ | $Na_2O$ |

In the case of the $Na^+$ ion sensor, the composition of the diffusion source 47 is determined beforehand such that the impurity layer 47 has the following composition.

$Na_2O$ or $Li_2O$: 10 to 25 mol%
$Al_2O_3$: 10 to 25 mol%
$SiO_2$: 50 to 80 mol%

In the case of the $K^+$ ion sensor, the composition of the diffusion source 47 is determined beforehand such that the impurity layer 47 has the following composition.

$Na_2O$ or $Li_2O$: 20 to 30 mol%
$Al_2O_3$: 1 to 10 mol%
$SiO_2$: 60 to 80 mol%

The film of the diffusion source 47 may be formed by the method of vapor depositing, spattering or the like compounds containing substance operative to react with substance constituting the lower surface stabilizing film 46 to form an ion exchange site sensitive to a given ion. Alternatively, the film of the diffusion source 47 may be formed by coating, spraying, spinner rotation coating, dipping or the like alcohol solution of an organic metal compound for forming the ion exchange site (alkoxyd solution). In the case of forming the film of the diffusion source 47 from the alkoxyd solution, the film thus formed is subjected to hydrolysis and then the heat treatment.

In the case of the $H^+$ ion sensor, as the alkoxyd compound, use may be made of $Si(OC_2H_5)_4$, 16 mol% solution of $Ca(OCH_3)_2$ and 16 mol% solution of $NaOCH_3$.

In the case of the Na+ and K+ ion sensor, as the alkoxyd compound, use may be made of $Si(OC_2H_5)_4$, $Al(i\text{-}OC_4H_9)_3$ and 16 mol% solution of $NaOCH_3$.

After the impurity layer 48 has been formed in the manner as above described, the diffusion source 47 remained on the surface stabilizing film 46 is removed to expose the impurity layer 48 as shown in FIG. 5B.

FIGS. 6A and 6B show another embodiment of an ion sensor and a method of manufacturing the same according to the invention. In the present embodiment, on the surface stabilizing film 46 is formed a separate inorganic film 49 having a thickness larger than 500 Å and in the surface of the inorganic film 49 is formed an impurity layer 48 by thermal diffusion. Such method is different from the method described with reference to FIGS. 5A and 5B. In FIGS. 6A and 6B, the same parts as those shown in FIGS. 5A and 5B are designated by the same reference numerals. That is, in the present embodiment, in the gate portion 41, on the gate insulating film 45 are formed the surface stabilizing film 46, inorganic film 49 and diffusion source film 47 superimposed one upon the other. Then, the gate portion 41 is heat treated to form the impurity layer 48 as shown in FIG. 6A. Subsequently, the diffusion source film 47 on the inorganic film 49 is removed to expose the impurity layer 48 as shown in FIG. 6B, thereby manufacturing an ion sensitive field effect transistor. In the present embodiment, the inorganic film 49 may be formed of a composition selected from the group consisting of oxide or nitride of silicon (Si), aluminum (Al), boron (B) or tantalum (Ta) and a mixture of such oxide and nitride.

Figure 7A:
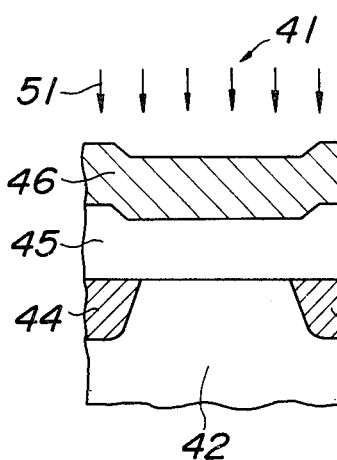
FIGS. 7A and 7B are diagrammatic cross-sectional views of essential parts of a further embodiment of an ion sensitive field effect transistor according to the invention manufactured by ion implantation.
Figure 7B:
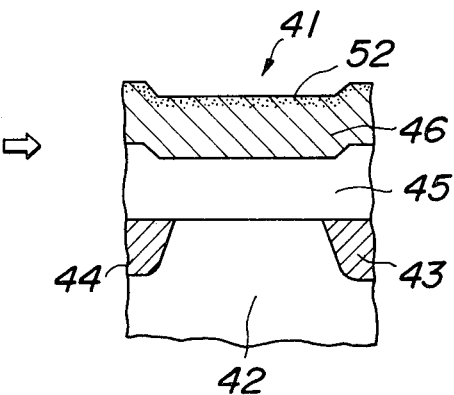

FIGS. 7A and 7B show a further embodiment of an ion sensor and a method of manufacturing the same according to the invention. In the present embodiment, an impurity atom 51 operative to react with the atom constituting the surface stabiizing film 46 to form an ion exchange site sensitive to a given ion is ion implanted into the surface of the inorganic surface stabilizing film 46 up to a depth on the order of several tens Å to several hundreds Å. Then, the surface stabilizing film 46 is annealed at 400° C. to 700° C. to form an impurity layer 52 operative as an ion sensitive region as shown in FIG. 7B. Such method is different from the method described with reference to FIGS. 5A and 5B. In FIGS. 7A and 7B, the same parts as those shown in FIGS. 5A and 5B are designated by the same reference numerals. An acceleration voltage applied in the case of effecting the ion implantation is different dependent on the kind of the impurity atom and depth of ion implantation (thickness of the impurity layer 52). But, it is preferable to use an acceleration voltage of about 100 to 300 KeV and an amount of ion dose on the order of $10^{16}$ to $10^{18}$ cm$^{-2}$. In addition, the impurity atom 51 to be subjected to the ion injection is different dependent on the kind of the ion sensor aimed at and the kind of the surface stabilizing film 46. In the case of the Na+ ion and K+ ion sensor, use may be made of the impurity atom 51 shown in the following Table 2, for example.

TABLE 2

| | Kind of surface stabilizing film 46 | | | |
|---|---|---|---|---|
| | Oxide, nitride of Si | Oxide, nitride of Al | Oxide, nitride of Ta | $SiO_2 + Al_2O_3$ |
| Impurity atom 51 | Na, Al, O | Na, Si, O | Na, Al, Si, O | Na |

Figure 8A:
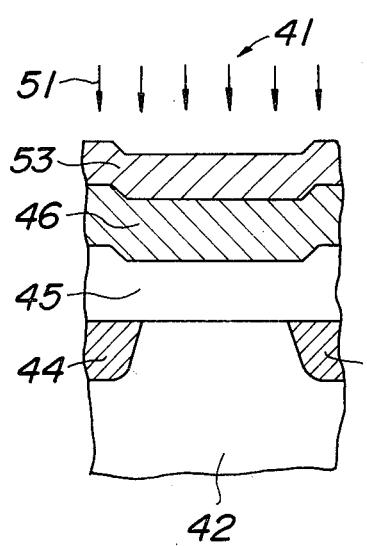
FIGS. 8A and 8B are diagrammatic cross-sectional views of essential parts of a still further embodiment of an ion sensitive field effect transistor according to the invention manufactured by ion implantation.
Figure 8B:
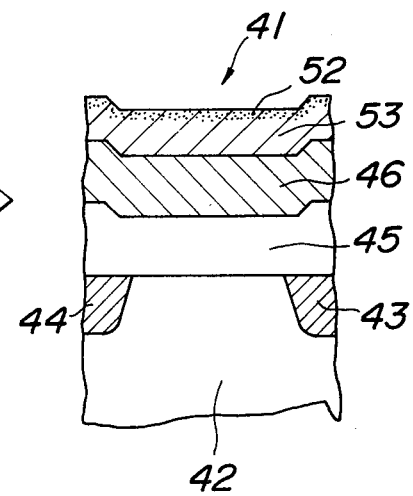

FIGS. 8A and 8B are diagrammatic cross-sectional views of essential parts of another embodiment of an ion sensor and a method of manufacturing the same according to the invention. In the present embodiment, on a surface stabilizing film 46 is formed a separate inorganic film 53. An impurity atom 51 operative to react with an atom constituting the inorganic film to form an ion exchange site sensitive to a given ion is ion implanted into the surface of the inorganic film 53 as shown in FIG. 8A. In the present embodiment, the method of forming the impurity layer 52 operative as the ion sensitive region is different from that described with reference to FIGS. 7A and 7B. The inorganic film 53 may be formed of a composition selected from the group consisting of oxide or nitride of silicon (Si), aluminum (Al), tantalum (Ta) and boron (B). In other case the film 53 may be selected from silver (Ag), copper (Cu), cadmium (Cd), lead (Pb) or the like and a mixture of these metals. For example, Cl−, Br−, S$^{2-}$ or the like may be ion implanted into the surface of silver (Ag) to convert the surface of silver into $AgCl+Ag_2S$, $AgBr+Ag_2S$. As a result, it is possible to provide an anion sensor which can detect Cl− ion and Br− ion. In the case of detecting the ions, use may be made of the impurity atom 51, composition of the inorganic film 53 and composition of the impurity layer 52 shown in the following Table 3.

TABLE 3

| | Ions to be detected | | | | | | |
|---|---|---|---|---|---|---|---|
| | CN− | Cl− | Br− | I− | Cu$^{2+}$ | Cd$^{2+}$ | Pb$^{2+}$ |
| Impurity atom 51 | I, S | Cl, S | Br, S | I, S | S | S | S |
| Inorganic film 53 | Ag | Ag | Ag | Ag | Ag + Cu | Ag + Cd | Ag + Pb |
| Impurity layer 52 | $AgI + Ag_2S$ | $AgCl + Ag_2S$ | $AgBr + Ag_2S$ | $AgI + Ag_2S$ | $Ag_2S + CuS$ | $Ag_2S + CdS$ | $Ag_2S + PbS$ |

In the embodiments shown in FIGS. 6 and 8, the inorganic films 49 and 53 have a relatively large thickness larger than 500 Å. But, in a still further embodiment shown in FIG. 9, provision is made of an inorganic film 55 having a relatively thin thickness on the order of 100 Å to 500 Å. In the present embodiment, an impurity layer 56 operative as an ion sensitive region is formed on substantially total surface of the inorganic film 55 by the thermal diffusion or ion implantation, thereby providing an ion sensitive field effect transistor.

Figure 10A:
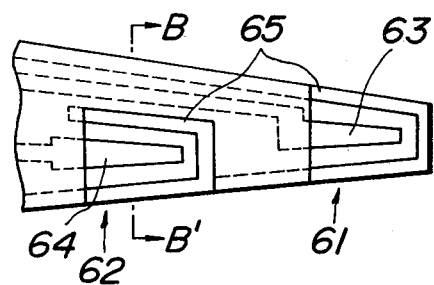
FIG. 10A is a diagrammatic plan view of a multiple ion sensitive field effect transistor according to the invention manufactured by thermal diffusion or ion implantation.
Figure 10B:
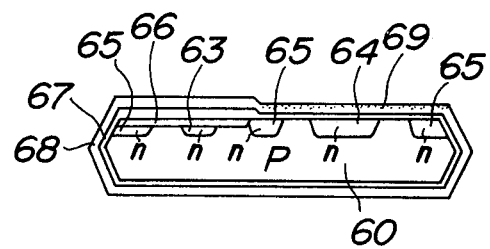
FIG. 10B is a section on line B—B' of FIG. 10.

In the present invention, a plurality of gate portions may be formed on the same semiconductor chip and impurity layers each operative as ion sensitive regions sensitive to different kinds of ions may be formed in the gate portions by thermal diffusion or ion implantation for the purpose of providing a multiple ion sensitive field effect transistor. FIG. 10A is a diagrammatic plan view of one embodiment of a multiple ion sensitive field effect transistor according to the invention. FIG. 10B is a section on line B—B' of FIG. 10A. The multiple ion sensitive field effect transistor comprises one semiconductor substrate 60 provided with two ion sensitive field effect transistors, one of which 61 operative as H+ ion sensor, whereas the other 62 operative as Na+ ion sensor.

Figure 9:
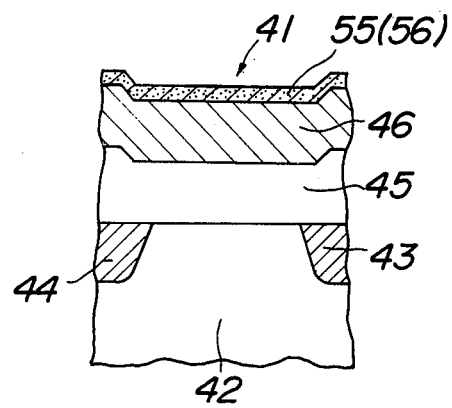
FIG. 9 is a diagrammatic cross-sectional view of essential parts of another embodiment of an ion sensitive field effect transistor according to the invention manufactured by thermal diffusion or ion implantation.

Each ion sensitive field effect transistor is provided with its own source diffusion regions 63, 64 and a common drain diffusion region 65 and provided at that portion which does not constitute the individual ion sensitive field effect transistor with a channel stopper 66. This multiple ion sensitive field effect transistor as a whole is covered with an insulating film 67 and an inorganic surface stabilizing film 68 superimposed one upon the other. In the surface layers of the surface stabilizing films 68 opposed to those portions of the ion sensitive field effect transistors 61 and 62 which include at least gate portions thereof are formed impurity layers 69 operative as H+ ion and Na+ ion sensitive regions by thermal diffusion or ion implantation (the impurity layer of the ion sensitive field effect transistor 61 is not shown in FIG. 10B). As shown in FIGS. 6, 8 and 9, the impurity layer may be formed in a separate inorganic film superimposed on the surface stabilizing film 68.

The ion sensitive field effect transistor manufactured by the method according to the invention will now be compared with the ion sensitive field effect transistor manufactured by the conventional method with reference to FIGS. 11A, 11B and 11C. FIG. 11A shows an infrared absorption characteristic obtained by measuring an infrared absorption spectrum of an ion sensitive field effect transistor comprising a silicon substrate having a thickness of 200 μm and provided thereon with an $Si_3N_4$ film (a surface stabilizing film) and an NAS film operative as an Na+ ion sensitive film superimposed one upon the other, the $Si_3N_4$ film having a thickness of about 1,000 Å and being formed by a chemical vapor deposition and the NAS film being formed from alcohol solution of an organic metal compound (alkoxyd solution). In FIG. 11A, the ordinate shows an infrared transmission strength and the abscissa shows the number of waves of the infrared spectrum. The NAS film was fired at 800° C. In FIG. 11A, the infrared absorption visible near the number of spectrum wave 830 $cm^{-1}$ (shown by an arrow A) was produced due to Si-N elongation and contraction oscillation of the $Si_3N_4$ film, whereas the infrared absorption visible near the number of spectrum wave 950 $cm^{-1}$ (shown by an arrow B) was produced due to Si-O elongation and contraction oscillation of the NAS film.

As seen from FIG. 11A, if the ion sensitive field effect transistor is immersed into 0.1 N HCl solution, the NAS film (the ion sensitive film) becomes effluent to gradually decrease the infrared absorption due to the Si-O elongation and contraction oscillation. The infrared absorption is completely eliminated after the lapse of several minutes to 10 minutes. This tendency is the same when the NAS film is fired at a temperature lower than 800° C.

FIGS. 11B and 11C show ion characteristics of the conventional ion sensitive field effect transistor and the ion sensitive field effect transistor according to the invention obtained by etching them by 0.1 N HCl solution and measuring interfacial potential $\Delta\phi Na$ with respect to Na+ ion and interfacial potential $\Delta\phi H$ with respect to H+ ion, respectively. In FIGS. 11B and 11C, the ordinate shows the interfacial potential $\Delta\phi$ and the abscissa shows the etching time.

The ion characteristic shown in FIG. 11B was obtained by the conventional ion sensitive field effect transistor shown in FIGS. 3A and 3B in which the surface stabilizing film is formed of $Si_3N_4$ and the ion sensitive film is formed by firing the NAS film at 500° C. The ion characteristic shown in FIG. 11C was obtained by the ion sensitive field effect transistor according to the invention, i.e. by firing the NAS film of the conventional ion sensitive field effect transistor shown in FIGS. 3A and 3B at 500° C. and then is subjected to a heat treatment at 800° C. for a short time to thermally diffuse a part of the composition of the NAS film into the lower $Si_3N_4$ film, thereby forming the impurity layer.

As can be seen from FIG. 11B, in the conventional ion sensitive field effect transistor in which the NAS film is merely superimposed on the $Si_3N_4$ film, if it is subjected to the etching treatment, the lower $Si_3N_4$ film is exposed, and as a result, the interfacial potential with respect to Na+ ion, that is, $\Delta\phi Na$ is decreased, whereas the interfacial potential with respect to H+ ion, that is, $\Delta\phi H$ is increased, thereby eliminating the ability of the Na+ ion sensor within a short time.

On the contrary, as can be seen from FIG. 11C, in the ion sensitive field effect transistor according to the invention in which one portion of the composition of the NAS film is thermally diffused into the $Si_3N_4$ film so as to form the impurity layer, even though the NAS film is disappeared within the etching time of several minutes to 10 minutes as explained with reference to FIG. 11A, the operation as the stable Na+ ion sensor is still maintained. This is because of the fact that the impurity layer consisting of one portion of the composition of the NAS film thermally diffused into the $Si_3N_4$ film constitutes the Na+ ion exchange site of $(Si-O-Al)^-$ and that the impurity layer in cooperation with the stable $Si_3N_4$ film (the surface stabilizing film) provides a stable ability.

In the case of measuring the infrared absorption characteristic shown in FIG. 11A and ion characteristics shown in FIGS. 11B and 11C, the NAS film (the ion sensitive film) was etched with a strong acid of 0.1 NHCl for the purpose of expedite the effluent of the NAS film. The same qualitative result was obtained even when the NAS film was subjected to the slow effluent in an electrolyte having a pH on the order of 7.

Experimental tests have shown the result that the conventional ion sensitive field effect transistor described with reference to FIG. 11B loses its ability as the Na+ ion sensor within 3 to 5 days, and that the ion sensitive field effect transistor according to the invention described with reference to FIG. 11C keeps its stable operative for more than 3 months.

As stated hereinbefore, the use of measures of forming the chemically stable inorganic film on the gate insulating film of the field effect transistor, and forming the impurity layer having a depth of several tens Å to several hundreds Å and operative as the ion sensitive region sensitive to the given ion by the thermal diffusion or ion injection so as to change the property of the surface of the inorganic film easily provides a novel ion sensitive field effect transistor which is long in life and uniform in characteristics. No attempt has heretofore been made to form the impurity layer operative as the ion sensitive region in the surface layer of the chemically stable inorganic film by the thermal diffusion or ion implantation. In this way, in the present invention, the impurity layer is formed on the surface layer of the inorganic film by the thermal diffusion or ion implantation, whereas in the conventional techniques, the ion sensitive film is merely superimposed on the inorganic film. As a result, the ion sensitive field effect transistor according to the invention has the advantages that any defect is not induced near the interface, that the surplus electric charge is not accumulated and hence the threshold value voltage of the field effect transistor is not changed and that it is possible to make the thickness of the gate portion as a whole thin so as to prevent the transfer conductance gm from being decreased, thereby obtaining a sufficiently large gain.

The invention is not limited to the above mentioned embodiments, but various changes and alternations may be made. For example, the diffusion source 47 formed on the surface stabilizing film 46 as shown in FIG. 5A and the diffusion source 47 formed on the inorganic film 49 as shown in FIG. 6A after the impurity layer 48 has been formed may be remained as it is.

The invention is particularly applicable to the ion sensitive field effect transistors, but may also be applicable to another type of ion sensor which make use of a semiconductor P-N diode.

What is claimed is:

1. A field effect transistor type ion sensor comprising an inorganic film formed on a gate insulating film of a field effect transistor, and an impurity layer formed in at least the surface layer of said inorganic film, and containing an impurity sensitive to a given ion, said impurity layer being operative as an ion sensitive region when it makes contact with a test substance, and said inorganic film is formed of a composition selected from the group consisting of silver (Ag), copper (Cu), cadmium (Cd) and lead (Pb).

2. A field effect transistor type ion sensor according to claim 1, wherein said inorganic film is formed through a surface stabilizing film on said gate insulating film.

3. A field effect transistor type ion sensor according to claim 1, wherein one semiconductor substrate is provided with a plurality of gate portions and impurity layers sensitive to different ions are formed in said gate portions, respectively.

* * * * *